US008841264B2

(12) United States Patent
Raederstorff et al.

(10) Patent No.: US 8,841,264 B2
(45) Date of Patent: Sep. 23, 2014

(54) COMPOSITIONS

(75) Inventors: Daniel Raederstorff, Flaxlanden (FR);
Nathalie Richard, Mulhouse (FR);
Joseph Schwager, Basel (CH); Karin Wertz, Rheinfelden (DE)

(73) Assignee: DSM IP Assets B.V., Heerlen (NL)

( * ) Notice: Subject to any disclaimer, the term of this patent is extended or adjusted under 35 U.S.C. 154(b) by 1129 days.

(21) Appl. No.: 12/373,584

(22) PCT Filed: Jul. 12, 2007

(86) PCT No.: PCT/EP2007/006188
§ 371 (c)(1),
(2), (4) Date: Nov. 4, 2009

(87) PCT Pub. No.: WO2008/006581
PCT Pub. Date: Jan. 17, 2008

(65) Prior Publication Data
US 2010/0056463 A1  Mar. 4, 2010

(30) Foreign Application Priority Data

Jul. 14, 2006 (EP) ..................................... 06014645

(51) Int. Cl.
| A01N 43/04 | (2006.01) |
| A61K 31/70 | (2006.01) |
| A01N 43/16 | (2006.01) |
| A61K 31/35 | (2006.01) |
| A01N 31/08 | (2006.01) |
| A61K 31/05 | (2006.01) |
| A01N 31/00 | (2006.01) |
| A61K 31/045 | (2006.01) |
| A01N 29/00 | (2006.01) |
| A61K 31/01 | (2006.01) |
| C07H 13/02 | (2006.01) |
| A61K 31/343 | (2006.01) |
| A61K 31/366 | (2006.01) |

(52) U.S. Cl.
CPC ............... *A61K 31/343* (2013.01); *A61K 31/05* (2013.01); *A61K 31/366* (2013.01)
USPC ............. 514/32; 514/451; 514/731; 514/738; 514/762; 536/119

(58) Field of Classification Search
CPC .. A61K 31/05; A61K 31/343; A61K 2300/00
See application file for complete search history.

(56) References Cited

U.S. PATENT DOCUMENTS

| 5,714,150 | A * | 2/1998 | Nachman ....................... 424/769 |
| 6,165,475 | A * | 12/2000 | Crea et al. .................... 424/769 |
| 6,197,308 | B1 * | 3/2001 | Crea et al. .................... 424/769 |
| 6,416,808 | B1 * | 7/2002 | Crea .............................. 426/601 |
| 6,437,004 | B1 * | 8/2002 | Perricone ..................... 514/738 |
| 6,468,553 | B1 | 10/2002 | Sheu et al. |
| 7,713,569 | B2 * | 5/2010 | Crea .............................. 426/601 |
| 7,741,500 | B2 * | 6/2010 | Arhancet et al. .................. 554/8 |
| 7,902,388 | B2 * | 3/2011 | Heise et al. .................... 554/224 |
| 8,057,835 | B2 * | 11/2011 | Makadia et al. .............. 426/601 |
| 8,158,681 | B2 * | 4/2012 | Raederstorff et al. ........ 514/559 |
| 8,216,599 | B2 * | 7/2012 | Crea .............................. 424/423 |
| 2004/0039066 | A1 * | 2/2004 | Crea .............................. 514/731 |
| 2008/0262081 | A1 * | 10/2008 | Raederstorff et al. ........ 514/457 |
| 2008/0300198 | A1 * | 12/2008 | Matt et al. ....................... 514/27 |
| 2010/0055218 | A1 * | 3/2010 | Raederstorff et al. ........ 424/765 |
| 2010/0113611 | A1 * | 5/2010 | Raederstorff et al. ........ 514/731 |
| 2011/0112201 | A1 * | 5/2011 | Liu et al. ....................... 514/731 |

FOREIGN PATENT DOCUMENTS

| DE | 101 31 057 | 1/2003 |
| JP | 2005-517033 T | 6/2005 |
| WO | 01/76579 | 10/2001 |
| WO | 01/83031 | 11/2001 |
| WO | 02/094193 | 11/2002 |
| WO | WO 03/068171 | 8/2003 |
| WO | 2006/020588 | 2/2006 |

OTHER PUBLICATIONS

International Search Report for PCT/EP2007/006188, mailed Apr. 11, 2008.
Written Opinion of the International Searching Authority for PCT/EP2007/006188, mailed Apr. 11, 2008.
Database WPI Week 200159, Derwent Publications Ltd., London, GB; AN 2001-530389, XP002414988.
Database WPI Week 200637, Derwent Publications Ltd., London, GB; AN 2006-360286, XP002414989.
Liu et al, "Phthalide Lactones from *Ligusticum chaunxiong* Inhibit Lipopolysaccharide-Induced TNF-α Production and TNF-α-Mediated . . . ", Planta Medica, 2005, vol. 71, No. 9, p. 808-813.
English translation of JP Office Action in JP 2009-519833 dated Sep. 4, 2012.

* cited by examiner

*Primary Examiner* — Lawrence E Crane
(74) *Attorney, Agent, or Firm* — Nixon & Vanderhye P.C.

(57) ABSTRACT

Compositions containing a combination of hydroxytyrosol and resveratrol or liqustilide or (−)-epigallocatechin gallate or honokiol or genistein or *Magnolia* bark extract or a combination of oleuropein and resveratrol or ligustilide are used to treat inflammatory disorders.

5 Claims, 1 Drawing Sheet

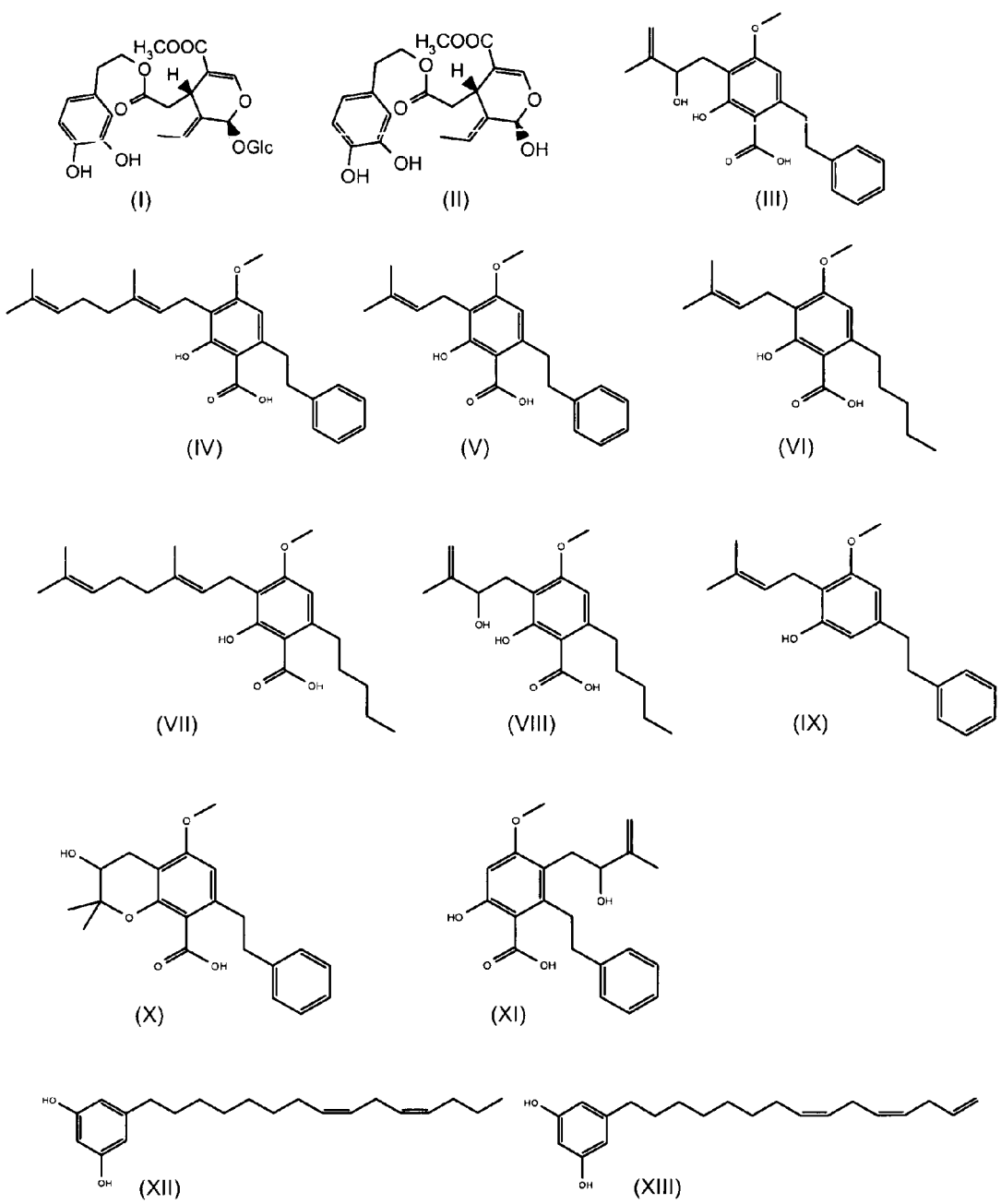

COMPOSITIONS

This application is the U.S. national phase of International Application No. PCT/EP2007/006188, filed 12 Jul. 2007, which designated the U.S. and claims priority to European Application No. 06014645.3, filed 14 Jul. 2006, the entire contents of each of which are hereby incorporated by reference.

The present invention relates to novel compositions comprising hydroxytyrosol and/or oleuropein (I) and at least one additional component selected from the group of ligustilide, oleuropein aglycone (II), tyrosol, extract from the bark of *Magnolia officinalis*, magnolol, honokiol, genistein, resveratrol, EGCG, methylsulfonylmethane, SAMe, collagen hydrolysate, collagen, ascorbyl phosphate, lycopene, lutein, zeaxanthin, β-cryptoxanthin, Devil's Claw, milk protein concentrate, solubilized keratin, celery seed extract, cetylated fatty acids, carnitine, thymoquinone, 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), cardol diene (XII), cardol triene (XIII), cashew fruit extract, boswellic acid, carnosic acid, ursolic acid, horse chestnut extract, diosmetin, tryptanthrin, diosgenin, curcumin and derivatives, *Glycyrrhiza foetida* and white willow bark extract as well as to the use of these compositions as a medicament, in particular as a medicament for the treatment, co-treatment or prevention of inflammatory disorders.

Inflammatory disorders are one of the most important health problems in the world. Inflammation is in general a localized protective response of the body tissues to invasion of the host by foreign material or injurious stimuli. The causes of inflammation can be infectious agents such as bacteria, viruses, and parasites; or physical agents such as burns or radiation; or chemicals like toxins, drugs or industrial agents; or immunological reactions such as allergies and autoimmune responses or conditions associated with oxidative stress.

Inflammation is characterized by pain, redness, swelling, heat, and eventual loss of function of the affected area. These symptoms are the results of a complex series of interactions mainly taking place between the cells of the immune system. The response of the cells results in an interacting network of several groups of inflammatory mediators: Proteins (e.g., cytokines, enzymes [e.g., proteases, peroxydase], major basic protein, adhesion molecules [ICAM, VCAM]), lipid mediators (e.g., eicosanoids, prostaglandins, leukotrienes, platelet activating factor [PAF]), reactive oxygen species (e.g., hydroperoxides, superoxyde anion $O_2-$, nitric oxide [NO] etc). However, many of those mediators of inflammation are also regulators of normal cellular activity. Thus, deficiencies of inflammatory reactions lead to a compromised host (i.e. infection) while uncontrolled and thus chronic inflammation leads to inflammatory diseases mediated in part by the excessive production of several of the above mentioned mediators.

Acute and chronic inflammation resulting from an excessive biosynthesis of inflammatory mediators is involved in numerous inflammatory disorders such as arthritis (e.g. osteoarthritis, rheumatoid arthritis), asthma, inflammatory bowel diseases, inflammatory diseases of the skin (e.g. contact dermatitis [particularly diaper area dermatitis], atopic dermatitis, xerosis, eczema, rosacea, seborrhea, psoriasis, neurodermitis, thermal and radiation burns such as sunburn, other types of skin inflammation, and the tissue-degenerating effects of aging) and chronic inflammatory disorders, such as atherosclerosis, heart diseases, metabolic syndrome X, cancer, Alzheimer's disease and pre-stages thereof such as mild cognitive impairment or photoageing which is associated with chronic skin inflammation.

Rheumatoid arthritis is a chronic inflammatory disease of the joints and is one of many different forms of arthritis. For example, arthritis includes rheumatoid arthritis, spondyloarthopathies, gouty arthritis, osteoarthritis, systemic lupus erythematosus and juvenile arthritis. Like asthma, rheumatoid arthritis is characterized at the molecular level by chronically unbalanced expression of cytokines, chemokines, kinins and their receptors, adhesion molecules and their respective receptors, as well as inflammatory enzymes.

Psoriasis is one of the most common skin problems, affecting 1-3% of the human population. Inflammatory bowel disease is a general term used to describe gastrointestinal tract diseases and includes disorders such as ulcerative colitis and Crohn's disease.

Beside the process of intravascular lipid deposition, inflammatory reactions of the endothelial (i.e. blood vessel) wall are considered to critically contribute to atherosclerosis i.e. atheroma formation. Atherosclerosis results from vascular injury which triggers inflammation. Activated macrophages, T-lymphocytes, and eventually smooth muscle cells are present in atherosclerotic plaques. Monocyte/macrophage and lymphocyte activation leads to the release of eicosanoids, cytokines and matrix metalloproteinases (MMPs) which are implicated in endothelial damage, as well as in the formation and eventually the rupture of atherosclerotic plaques. Finally, circulating inflammatory markers such as C-reactive protein (CRP), fibrinogen, and interleukins are increased or altered in groups at high-risk of coronary artery diseases (CAD). Several clinical trials indicate that elevated CRP concentration correlates with increased risk of coronary, and vascular events. Thus inflammation appears to play an important role in the initiation and progression of atheroma formation.

Inflammatory processes are also associated with the pathophysiology of Alzheimer's disease. There is evidence of inflammation in the brain of patients with Alzheimer's disease, as it is characterized by increased levels of cytokines and activated microglial cells. Thus, inflammation is not only involved in the classical inflammatory disorders (e.g., arthritis, asthma, bowel diseases) but is also associated with many chronic inflammatory disorders (e.g., atherosclerosis, heart diseases, metabolic syndrome X, cancer, Alzheimer disease).

Inflammatory events are also associated with the pathophysiology of different types of cancers (e.g. gastric and intestinal cancers, melanomas). Increased levels of inflammatory mediators such as prostaglandins have been found in cancers of breast, colon, lung and pancreas in humans.

Currently, two main classes of drugs, the corticosteroid and the nonsteroidal anti-inflammatory drugs (NSAIDs) are used to treat inflammatory disorders. NSAIDs and corticosteroids provide essentially symptomatic relief. Use of corticosteroids has declined due to a growing concern about the serious side effects of prolonged use.

NSAIDs are among the most widely used drugs, primarily for the treatment of pain and inflammatory disorders, in particular for the treatment of arthritis (i.e. pain relief). Epidemiological studies have suggested that patients taking NSAIDs have a lower risk of developing Alzheimer's disease than those not taking NSAIDs. A protective effect of NSAIDs suggests that the cyclooxygenases might be involved in the neurodegenerative process. Epidemiological studies showed a significant reduction in the risk of colorectal, gastric, esophageal, and breast cancers among people who take NSAIDs compared with those not taking NSAIDs. In animal models, NSAIDs significantly reduced tumor development.

However, long-term use of NSAIDs when treating chronic diseases such as arthritis, is limited by severe side-effects like serious gastrointestinal complications, renal toxicity or asthmatic reactions.

Therefore, there is a need for new anti-inflammatory agents with weak or no side effects. Patients with inflammatory diseases have a special interest in a type of treatment considered as "natural" with mild anti-inflammatory effects and without major side effects, which can be used for disease prevention and as adjuvant treatment. Furthermore, the treatment used needs to maintain the equilibrium between excessive and insufficient inflammatory reaction.

There are many known examples of such "natural" agents with shown anti-inflammatory action. However, a disadvantage of these "natural" compounds is that their biological and thus inhibitory activity is often inadequate. When two or more natural substances are applied concomitantly, their action can be additively or even synergistically enhanced. This lowers the required amount of each substance in order to effect disease development or treatment. Since lower doses of each of the natural substances individually can be used, there is less chance that deleterious levels are reached and also less chance of serious side-effects due to chronic use.

The invention relates to a composition comprising hydroxytyrosol and/or oleuropein (I), in particular hydroxytyrosol, and at least one additional component selected from the group of ligustilide, oleuropein aglycone (II), tyrosol, extract from the bark of Magnolia officinalis, magnolol, honokiol, genistein, resveratrol, EGCG, methylsulfonylmethane, SAMe, collagen hydrolysate, collagen, ascorbyl phosphate, lycopene, lutein, zeaxanthin, β-cryptoxanthin, Devil's Claw, milk protein concentrate, solubilized keratin, celery seed extract, cetylated fatty acids, carnitine, thymoquinone, 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), cardol diene (XII), cardol triene (XIII), cashew fruit extract, boswellic acid, carnosic acid, ursolic acid, horse chestnut extract, diosmetin, tryptanthrin, diosgenin, curcumin and derivatives, Glycyrrhiza foetida and white willow bark extract. Preferably, the invention relates to a composition comprising hydroxytyrosol and/or oleuropein (I), in particular hydroxytyrosol, and at least one additional component selected from the group of ligustilide, oleuropein aglycone, magnolol, honokiol, genistein, resveratrol, EGCG, magnolia bark extract, cashew fruit extract and Glycyrrhiza foetida. Even more preferably, the invention relates to a composition comprising hydroxytyrosol and/or oleuropein (I), in particular hydroxytyrosol, and at least one additional component selected from the group of ligustilide, magnolol, genistein, resveratrol, EGCG, magnolia bark extract, cashew fruit extract and Glycyrrhiza foetida. In a most preferred embodiment, the invention relates to a composition comprising hydroxytyrosol and/or oleuropein (I), in particular hydroxytyrosol, and at least one additional component selected from the group of ligustilide, honokiol, genistein, resveratrol and EGCG.

Thus in one preferred embodiment the invention relates to a composition comprising hydroxytyrosol and/or oleuropein (I) and ligustilide, most preferably to a composition comprising hydroxytyrosol and ligustilide or a composition comprising oleuropein and ligustilide.

In another preferred embodiment the invention relates to a composition comprising hydroxytyrosol and/or oleuropein (I) and honokiol, most preferably to a composition comprising hydroxytyrosol and honokiol. Most preferably, honokiol is used in the form of an extract from the bark of Magnolia officinalis comprising honokiol and magnolol.

In a further preferred embodiment the invention relates to a composition comprising hydroxytyrosol and/or oleuropein (I) and genistein, most preferably to a composition comprising hydroxytyrosol and genistein.

In an additional preferred embodiment the invention relates to a composition comprising hydroxytyrosol and/or oleuropein (I) and resveratrol, most preferably to a composition comprising hydroxytyrosol and resveratrol or a composition comprising oleuropein and resveratrol.

In a further preferred embodiment the invention relates to a composition comprising hydroxytyrosol and/or oleuropein (I) and EGCG, most preferably to a composition comprising hydroxytyrosol and EGCG.

In all of the above mentioned embodiments preferably the molar ratio of hydroxy-tyrosol, respectively oleuropein to the additional ingredient is about 1 to 1.

In another preferred embodiment the invention relates to a composition comprising hydroxytyrosol and/or oleuropein (I), in particular hydroxytyrosol, and lycopene and resveratrol. Particular preferred are compositions wherein the molar ratio of lycopene is smaller than the molar amount of resveratrol and of hydroxytyrosol and the molar amount of resveratrol and hydroxytyrosol is equal. Most preferably, the molar ratio of lycopene to resveratrol to hydroxytyrosol is in the range of about 1:2:2 to 1:10:10, in particular 1:4:4 to 1:8:8, most in particular in the range of 1:6:6.

It has surprisingly been found that the individual components in the composition of the present invention function synergistically in their anti-inflammatory activity. Moreover, the composition of the present invention may be especially useful in the treatment, co-treatment and prevention of inflammatory disorders, such as heart disease, multiple sclerosis, osteo- and rheumatoid arthritis, atherosclerosis, and osteoporosis.

The composition of the present invention is especially suitable for the treatment, co-treatment and prevention of different forms of arthritis, in particular osteoarthritis and rheumatoid arthritis. Also, the composition of the present invention is suitable as an agent for treatment, co-treatment and prevention of joint disorders in particular for reduction of joint inflammation, maintenance and/or increase of joint health, prevention of joint stiffness, increase of joint mobility, providing supple and/or flexible joints, lubrication of the joints, relief of pain associated with joint inflammation, decrease of joint swelling, lessening joint problems, and providing joint care. Thus, the invention also relates to the use of a composition of the invention as an agent for the treatment, co-treatment or prevention of inflammatory disorders as well as joint disorders.

In a different aspect, the invention also relates to the composition of the invention for use as a medicament.

In yet another embodiment, the invention relates to the use of a composition according to the invention for the manufacture of a nutraceutical, pharmaceutical, cosmetic or dermatological preparation suitable for the treatment, co-treatment or prevention of inflammatory disorders, more preferably of arthritis or skin inflammation, most preferably of osteoarthritis or sunburn.

Also, the invention relates to a method for treatment, co-treatment and prevention of inflammatory disorders, in particular of arthritis, more in particular of osteoarthritis or rheumatoid arthritis, in animals including humans said method comprising the step of administering 'an effective amount of the composition according to the invention' to animals including humans, which are in need thereof. Preferably, the inflammatory disorder is arthritis, most preferably osteoarthritis.

The term 'an effective amount of the composition according to the invention' refers to an amount necessary to obtain a physiological effect. The physiological effect may be achieved by one single dose or by repeated doses. The dosage administered may, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired and can be adjusted by a person skilled in the art.

In the framework of the invention, with animals is meant all animals, including mammals, examples of which include humans. Preferred examples of mammals beside humans are non-ruminant or ruminant animals including cats, dogs, dromedaries, camels, elephants, and horses.

In another embodiment the invention relates to a nutraceutical composition comprising the composition according to the invention and a nutraceutically acceptable carrier.

The term nutraceutical composition as used herein include food product, foodstuff, dietary supplement, nutritional supplement or a supplement composition for a food product or a foodstuff.

Thus, in another embodiment the present invention relates to a nutraceutical wherein the nutraceutical is a food product, foodstuff, dietary supplement, nutritional supplement or a supplement composition for a food product or a foodstuff.

As used herein, the term food product refers to any food or feed suitable for consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to any substance fit for human or animal consumption. The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term nutritional supplement refers to a composition comprising a dietary supplement in combination with a source of calories. In some embodiments, nutritional supplements are meal replacements or supplements (e.g., nutrient or energy bars or nutrient beverages or concentrates).

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

The term food products or foodstuffs also includes functional foods and prepared food products, the latter referring to any pre-packaged food approved for human consumption.

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of hydroxytyrosol and/or oleuropein (I) and the at least one additional component administered via a nutraceutical will, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation of a nutraceutical composition.

In a preferred embodiment, the nutraceutical comprises per serving an amount of 0.01 to 1 g, more preferably 0.2 mg to 500 mg of hydroxytyrosol and/or oleuropein (I) and at least one component selected from
- Ligustilide: 0.5 to 500 mg and/or
- Honokiol and/or Magnolol: 0.2 mg to 500 mg of each, preferably in the form of a magnolia bark extract and/or
- Genistein: 0.5 to 500 mg and/or
- Resveratrol: 0.2-500 mg, and/or
- EGCG: 2.0 to 500 mg and/or
- Cardol diene (XII) and/or cardol triene (XIII): 0.2 to 1000 mg of each, preferably in the form of a cashew fruit extract (*Anacardium occidentale*) and/or
- *Glycyrrhiza foetida* or one or several compounds selected from formula (III) to (XI): 0.5-1000 mg of each, preferably in the form of a *Glycyrrhiza foetida* extract in the indicated amounts.

In another aspect, the invention relates to a pharmaceutical comprising the composition according to the invention and a pharmaceutically acceptable carrier.

A person skilled in the art knows which carriers can be used as pharmaceutically acceptable carriers. Suitable pharmaceutical carriers are e.g. described in Remington's Pharmaceutical Sciences, supra, a standard reference text in this field. Examples of such pharmaceutically acceptable carriers are both inorganic and organic carrier materials, suitable for oral/parenteral/injectable administration and include water, gelatin, gum arabic, lactose, starch, magnesium stearate, talc, vegetable oils, and the like.

The pharmaceutical composition may further comprise conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

In a preferred embodiment the pharmaceutical is in the form of a powder, tablet, capsule, gel, liquid or solid embodiment.

The dosages and ratios of the individual components in a pharmaceutical composition can be determined by the expert in the field with normal preclinical and clinical trials, or with the usual considerations regarding the formulation of pharmaceutical composition.

In a preferred embodiment hydroxytyrosol and/or oleuropein (I) is administered via a pharmaceutical composition either in the form of a single dose or by multiple doses in an amount of at least 0.3 mg/kg bodyweight/day, preferably in an amount of 1-450 mg/kg body weight/day, most preferably in an amount of 4-140 mg/kg body weight/day.

The nutraceutical and pharmaceutical according to the present invention may be in any galenic form that is suitable for administering to the animal body including the human body, more in particular in any form that is conventional for oral administration, e.g. in solid form, for example as (additives/supplements for) food or feed, food or feed premixes, fortified food or feed, tablets, pills, granules, dragées, capsules, and effervescent formulations such as powders and tablets, or in liquid form, for instance in the form of solutions, emulsions or suspensions, for example as beverages, pastes and oily suspensions. The pastes may be filled into hard or soft shell capsules. Examples for other application forms are forms for transdermal, parenteral, topical or injectable administration. The nutraceutical and pharmaceutical may be in the form of controlled (delayed) release formulation. Examples of pharmaceuticals also include compositions suitable for topical application such as crèmes, gels, sprays, dry sticks, powders etc.

The term hydroxytyrosol relates to 'pure hydroxytyrosol' of either synthetic origin or obtainable from natural sources such as from products and by-products derived from the olive tree by extraction and/or purification. Additionally the term hydroxytyrosol encompasses hydroxytyrosol comprising extracts obtainable e.g. from products and by-products derived from the olive tree.

Products and by products of olive trees encompass olives, olive tree leafs, olive pulps, olive oil, olive-derived vegetation water and olive oil dregs without being limited thereto. Based on the extraction procedure the amount, respectively the ratio of the hydroxytyrosol can be easily adjusted by a person skilled in the art. Preferably, hydroxytyrosol is derived from olives that may be obtained from conventional and commercially available sources such as growers.

In case of synthetic or purified hydroxytyrosol, the term 'pure hydroxytyrosol' relates to hydroxytyrosol having a purity of at least 90%, more preferably a purity of at least 91%, even more preferably a purity of at least 92%, even more preferably a purity of at least 93%, even more preferably a purity of at least 94%, even more in particular a purity of at least 95%, in particular a purity of at least 96%, more in particular a purity of at least 97%, even more in particular a purity of at least 98%, most in particular a purity of at least 99%. The purity of hydroxytyrosol can be determined by methods known to a person skilled in the art such as e.g. by HPLC, or LC-MS.

The hydroxytyrosol employed herein can be prepared by a number of methods known in the art. The olives may be processed by any suitable means to obtain the compositions described. For example, the olives and/or olive leaves may be pressed to obtain a mixture including olive oil, vegetation water and solid byproducts. The hydroxytyrosol may be obtained directly from the mixture or the mixture may be fractionated and/or purified to obtain the hydroxytyrosol. The compositions may be fractionated and/or purified by a number of methods known to the person skilled in the art. Examples of fractionating methods include partitioning with an organic solvent, chromatography, for example high pressure liquid chromatography (HPLC) or the use of supercritical fluids.

Examples of references that deal with the extraction of hydroxytyrosol from olive leaves are WO02/18310 A1, US 2002/0198415 A1, WO2004/005228 A1, U.S. Pat. No. 6,416,808 and US 2002/0058078 A1 which disclose a method for acidic hydrolysis of olive vegetation water for 2 to 12 months until at least 90% of the present oleuropein has been converted. A method of extraction of hydroxytyrosol from olives, olive pulps, olive oil and oil mill waste water is described by Usana Inc. U.S. Pat. No. 6,361,803 and WO01/45514 A1 and in US 2002/0004077 A1. EP 1 582 512 A1 describes an extraction of hydroxytyrosol from olive leaves. A method for obtaining hydroxytyrosol from the vegetation water of de-pitted olives is disclosed in US 2004/0039066 A1 in paragraphs [0080]-[0091].

Commercially available hydroxytyrosol containing olive extracts which may be used according to the invention include e.g. extracts from olive fruits such as Polyphen-Oil™ from Life Extension, OleaSelect™ from Indena, Hytolive® from Genosa, Prolivols from Seppic, OLIVE LEAF or OLIVE Water Extract of *Olea europea* from Lalilab, Hitofulvic and Olife™ from Ebiser, hydrolysed olive leaf extract, such as described in EP1582512, olive leaf extract, rich in oleuropein, such as available from Furfural and HIDROX® from CreAgri.

Preferably HIDROX® from CreAgri such as HIDROXO® 2% spray dried powder, HIDROX® Gold freeze dried powder (9%) and HIDROX® 6% freeze dried powder organic olive juice extract are used.

An example of a synthetic process in which hydroxytyrosol may be prepared with a purity >90% is a process comprising the steps of hydrogenating 3,4-dihydroxymandelic acid or a 3,4-dihydroxymandelic acid $C_{1-10}$-alkyl ester in a $C_{1-10}$-alkanol in the presence of a precious metal hydrogenation catalyst and optional reduction of the formed (3,4-dihydroxyphenyl)-acetic acid $C_{1-10}$-alkyl ester is to form 2-(3,4-dihydroxyphenyl)-ethanol (=hydroxytyrosol) a specific example of which is described below.

The hydrogenation may be carried out in the presence of a precious metal catalyst such as Pd and Rh, separately or in mixtures, in a manner known per se. In order to increase the activity and stability of the catalysts they are preferably used on carriers such as activated carbon, alumina or kieselguhr. The preferred hydrogenation catalyst in the present case is Pd/C.

The hydrogenation is carried out in the presence of a lower alkanol, i.e. a $C_{1-10}$-alkanol, such as methanol, ethanol, propanol, isopropanol, butanol, preferably in methanol or ethanol, preferably in the presence of a strong acid, preferably hydrochloric acid, preferably at a temperature from ambient temperature to 100° C. or higher, preferably from 40-65° C., preferably at a hydrogen pressure at least higher than the vapor pressure of the solvent at the hydrogenation temperature. The pressure can be from normal, i.e. atmospheric pressure, to 100 bar or higher.

If desired, the reaction which is preferably carried out as a through process can be accomplished in two separate steps, i.e., a first step wherein an ester of 3,4-dihydroxymandelic acid is built by esterification of the acid and a second step wherein the 3,4-dihydroxymandelic acid lower alkyl ester is hydrogenated. The reduction of the (3,4-dihydroxyphenyl)-acetic acid $C_{1-10}$-alkyl ester to give hydroxytyrosol can be achieved in a known manner. The preferred reduction agents are complex hydrids of aluminum and boron, such as $LiAlH_4$ and $NaBH_4$. The starting material, 3,4-dihydroxymandelic acid, is well-known and can be prepared in accordance with methods described in the literature, e.g., by condensation of catechol with glyoxylic acid.

Preferably hydroxytyrosol is used in the form of a hydroxytyrosol containing olive extract.

Hydroxytyrosol is used in an amount of sufficient to administer to animals including humans (e.g. weighing about 70 kg) a dosage of at least 0.02 mg/day. Preferably hydroxytyrosol is used in a concentration so that the daily consumption by an animal including humans (e.g. weighing about 70 kg) is in the range of from 1 mg/day to 2000 mg/day, more preferably from 5 mg/day to 500 mg/day. Thus, the daily dosage is at least about 0.3 µg/kg body weight, preferably an average dosage of 0.01-30 mg/kg body weight, most preferable of 0.1-10 mg/kg of bodyweight is used.

A nutraceutical composition preferably comprises 0.2 mg to 500 mg of hydroxytyrosol per serving, preferably 1 mg to 250 mg. If the composition is a pharmaceutical composition such composition may for example comprise hydroxytyrosol in an amount from 1 mg to 500 mg per dosage unit, e.g., per capsule or tablet, or from 1 mg per daily dose to 500 mg per daily dose of a liquid formulation.

If instead of 'pure hydroxytyrosol' a hydroxytyrosol comprising extract is used, the amount of the extract to be used may be derived from the concentration of 'pure hydroxytyrosol' within the extract and the finding of the optimal dosage is a matter of routine experimentation for the person skilled in the art.

The phenolic compounds oleuropein (I), oleuropein aglycone (II) and/or tyrosol may either be of synthetic origin or may be obtained from natural sources such as from products and by-products derived from the olive tree by extraction and/or purification. Products and by products of olive trees encompass olives, olive tree leafs, olive pulps, olive oil, olive-derived vegetation water and olive oil dregs without being limited The phenolic compounds oleuropein (I), oleuropein aglycone (II) or tyrosol employed herein can be prepared by a number of methods known in the art. E.g. the compounds may be derived from olives which may be processed by any suitable means to obtain the compounds described. For example, the olives and/or olive leaves may be pressed to obtain a mixture including olive oil, vegetation water and solid byproducts. The phenolic compounds may be obtained directly from the mixture or the mixture may be fractionated and/or purified to obtain the phenolic compounds. The compositions may be fractionated and/or purified by a number of methods known to the person skilled in the art. Examples of fractionating methods include partitioning with an organic solvent, chromatography, for example high pressure liquid chromatography (HPLC) or the use of supercritical fluids.

The phenolic compounds oleuropein (I), oleuropein aglycone (II) or tyrosol or mixtures thereof are preferably used in a concentration so that the daily consumption by an animal including humans (e.g. weighing about 70 kg) is in the range of from 1 mg/day to 2000 mg/day, more preferably from 5 mg/day to 500 mg/day. A nutraceutical composition preferably comprises 0.2 mg to 500 mg of phenolic compound per serving. If the composition is a pharmaceutical composition such composition may for example comprise a phenolic compound in an amount from 1 mg to 2000 mg per dosage unit, e.g., per capsule or tablet, or from 1 mg per daily dose to 3000 mg per daily dose of a liquid formulation.

Ligustilide may be isolated by methods known in the art [see, e.g., Beck J. J. and Stermitz F. R., J. Natural Products, Vol. 58, No. 7, pp. 1047-1055, 1995] from various plants such as *Angelica glauca, Angelica acutiloba, Angelica sinensis, Angelicae dahuricae, Ligusticum acutilobum, Ligusticum officinale, Ligusticum sinense, Ligusticum wallichii, Cnidium officinale, Rhizoma Chuanxiong, Pleurospermum hookeri, Trachyspermum roxburghianum, Meum athamanticum, Lomatium torreyi, Scutellaria baicalensis, Opopanax chironium, Cenolophium denudatum, Coriandrum sativuum, Silaum silaus*, but may also be synthesized by methods known in the art. Preferably ligustilide is used in form of a purified plant extract, e.g., from *Ligusticum* species, especially *L. wallichii*, comprising at least 50 wt.-% of ligustilide, and no more than 10 wt.-% of fatty acids and triglycerides as obtainable by the process disclosed in European patent application No. 05 002333.2, the contents of which are incorporated herein by reference.

Preferably ligustilide is used in an effective dose of 0.01 to 50 mg/kg body weight/day, more preferably 0.1 to 5 mg/kg body weight/day.

A nutraceutical preferably comprises 0.5 mg to 500 mg of ligustilide per serving. If the composition is a pharmaceutical, such composition may preferably comprise ligustilide in an amount from 1 mg to 500 mg per dosage unit, e.g., per capsule or tablet, or from 1 mg per daily dose to 2000 mg per daily dose of a liquid formulation.

The term "magnolol" as used herein comprises the pure compound also known as 5,5'-Diallyl-2,2'-biphenyldiol or 5,5'-di-2-propenyl-[1,1'-Biphenyl]-2,2'-diol (CAS [528-43-8]) and plant extracts containing the same. The term magnolol also comprises etherified or esterified hydroxy derivatives from 5,5'-Diallyl-2,2'-biphenyldiol or 5,5'-di-2-propenyl-[1, 1'-Biphenyl]-2,2'-diol. The ester or ether groups may for example be derived from straight or branched alkyl groups having 1 to 26 carbon atoms or from substituted or unsubstituted straight or branched aliphatic, araliphatic or aromatic carboxylic acids having 1 to 26 carbon atoms. Examples of etherified hydroxy groups further include glycoside groups. Examples of esterified hydroxy group further include glucuronide or sulfate groups. Preferably magnolol as used herein is 5,5'-Diallyl-2,2'-biphenyldiol or 5,5'-di-2-propenyl-[1,1'-Biphenyl]-2,2'-diol.

Plant extracts containing the compound include extracts from *Magnolia officinalis, Magnolia obovata, Magnolia rostrata, Magnolia bilboa, Magnolia biondii, Magnolia quinquepeta, Magnolia sprengeri, Manglietia insignis, Manglietia szechuanica, Manglietia yuyuanensis, Cercidiphyllum japonicum* and others. Magnolol is a known anti-inflammatory agent and is preferably used in the form of an extract from the bark of *Magnolia officinalis*, but may of course also be used in pure form.

Magnolol is preferably used in a concentration so that the daily consumption by an animal including humans (e.g. weighing about 70 kg) is in the range of from 1 mg/day to 2000 mg/day, preferably from 5 mg/day to 500 mg/day. A nutraceutical preferably comprises 0.2 mg to 500 mg of magnolol per serving. A pharmaceutical may for example comprise magnolol in an amount from 1 mg to 500 mg per dosage unit, e.g. per capsule or tablet, of from 5 mg daily dose to 2000 mg per daily dose of a liquid formulation.

The term "honokiol" as used herein comprises the pure compound also known as 3',5-Diallyl-2,4'-biphenyldiol or 3',5-di-2-propenyl-[1,1'-Biphenyl]-2,4'-diol (CAS [35354-74-6]) and plant extracts containing the same.

The term honokiol also comprises etherified or esterified hydroxy derivatives from 3',5-Diallyl-2,4'-biphenyldiol or 3',5-di-2-propenyl-[1,1'-Biphenyl]-2,4'-diol. The ester or ether groups may for example be derived from straight or branched alkyl groups having 1 to 26 carbon atoms or from substituted or unsubstituted straight or branched aliphatic, araliphatic or aromatic carboxylic acids having 1 to 26 carbon atoms. Examples of etherified hydroxy groups further include glycoside groups. Examples of esterified hydroxy group further include glucuronide or sulfate groups. Preferably, "honokiol" as used herein is 3',5-Diallyl-2,4'-biphenyldiol or 3',5-di-2-propenyl-[1,1'-Biphenyl]-2,4'-diol.

Plant extracts containing the compound include extracts from *Magnolia officinalis, Magnolia obovata, Magnolia rostrata, Magnolia bilboa, Magnolia biondii, Magnolia quinquepeta, Magnolia sprengeri, Manglietia insignis, Manglietia szechuanica, Manglietia yuyuanensis, Cercidiphyllum japonicum, Machilus thunbergii* and others. Honokiol is a known anti-inflammatory agent and is preferably used in the form of an extract from the bark of *Magnolia officinalis*, buy may of course also be used in pure form.

Honokiol is preferably use in a concentration so that the daily consumption by an animal including humans (e.g. weighing about 70 kg) is in the range of from 1 mg/day to 2000 mg/day, preferably from 5 mg/day to 500 mg/day. A nutraceutical preferably comprises 0.2 mg to 500 mg of honokiol per serving. A pharmaceutical may for example comprise honokiol in an amount from 1 mg to 500 mg per dosage unit, for example per capsule or table, or from 5 mg per daily dose to about 2000 mg per daily dose of a liquid formulation.

*Magnolia* bark (optionally in dried or ground form) may be extracted conventionally with solvents like ethanol, dichloromethane at reflux temperature or at lower temperature. Alternatively, it may be extracted with supercritical fluids like SF carbondioxyde or by steam distillation of the bark with water followed by sampling of the distilled organic part. Sampling may for example be done by extraction with an organic solvent like dichloromethane. Subsequent removal of the solvent gives the desired magnolia bark extract. Optionally the thus obtained magnolia bark extract may be subjected to further processing steps to enrich the content of magnolol and/or honokiol to give an extract of magnolia bark enriched in magnolol and/or honokiol.

Most preferably in all embodiments of the invention an extract derived from the bark of *Magnolia officinalis* comprising magnolol as well as honokiol is used in all embodiments of the invention.

The term "genistein" as used herein comprises the aglycone (4',5,7-trihydroxyisoflavone) and derivatives thereof, e.g., genistein glycosides, genistein sulfates, genistein glucuronides.

Genistein is preferably used in a concentration so that the daily consumption by an animal including humans (e.g. weighing about 70 kg) is in the range of from 0.5 mg/day to 2000 mg/day. A nutraceutical preferably comprises for example 0.2 mg to 500 mg of genistein per serving. A pharmaceutical composition may for example comprise a genistein in an amount from 0.5 mg to 500 mg per dosage unit, e.g., per capsule or tablet, or from 0.5 mg per daily dose to 2000 mg per daily dose of a liquid formulation.

The term "resveratrol" as used herein comprises a derivative, metabolite or analogue thereof. The carbon-carbon double bond may be trans or cis and includes cis/trans mixtures. Etherified or esterified hydroxy groups may be derived from unsubstituted or substituted, straight or branched chain alkyl groups having 1 to 26 carbon atoms or from unsubstituted or substituted, straight or branched chain aliphatic, araliphatic or aromatic carboxylic acids having 1 to 26 carbon atoms. Etherified hydroxy groups may further be glycoside groups and esterified hydroxy groups may further be glucuronide or sulfate groups. Of primary interest for the purposes of the invention is (trans)-resveratrol.

Resveratrol is preferably used in amount sufficient to administer to an animal including humans (e.g. weighing about 70 kg) a dosage from 0.5 mg/day to 2000 mg/day, more preferably from 5 mg/day to 500 mg/day. Thus, if the composition is a nutraceutical composition the amount of a resveratrol comprised therein is preferably in the range from 0.2 mg to 500 mg per serving. If the composition is a pharmaceutical composition such composition may preferably comprise from 0.5 mg to 500 mg per solid dosage unit, e.g., per capsule or tablet, or from 0.5 mg per daily dose to 2000 mg per daily dose of a liquid formulation.

The term "EGCG" as used herein comprises (−)-epigallocatechin gallate (EGCG in the narrower sense) and/or one or more derivatives (esterified forms, glycosides, sulphates) thereof, or other catechins found in green tea such as (−) epigallocatechin (EGC), (−) epicatechin-3-gallate (ECG), (−) epicatechin (EC), (+) gallocatechin, and (+) catechin and derivatives thereof. Of primary interest for use in the present invention is (−)-epigallocatechin gallate.

EGCG is preferably used in a concentration so that the daily consumption by an animal including humans (e.g. weighing about 70 kg) is in the range of from 5 mg/day to 2000 mg/day, preferably from 20 mg/day to 300 mg/day. A nutraceutical composition preferably comprises from 2 mg to 500 mg of EGCG per serving. If the composition is a pharmaceutical composition such composition may comprise EGCG for example in an amount from 5 mg to 500 mg per dosage unit, for example per capsule or tablet, or from 10 mg per daily dose to 2000 mg per daily dose of a liquid formulation.

The term boswellic acid encompasses pure boswellic acid and derivatives thereof as well as extracts comprising boswellic acid. Boswellic extract comprising e.g. 3-O-acetyl-11-keto-beta-boswellic acid, are known to the person skilled in the art. For instance, it is available on the market in a dietary supplement called 5-LOXIN® (company PL Thomas). The extract itself it available as WokVel® from Geni Herbs. It may be extracted from *Boswellia serrata*.

The daily intake by a human adult (weighing approximately 70 kg) of boswellic acid (extracts) is preferably between 5 and 1000 mg per day, preferably between 100 and 500 mg per day.

A nutraceutical composition preferably comprises between 5 mg and 500 mg of boswellic acid or boswellic acid extract per serving. If the composition is a pharmaceutical composition such composition may preferably comprise boswellic acid or boswellic acid extract in an amount from 50 mg to 500 mg per dosage unit, e.g., per capsule or tablet, or from 50 mg per daily dose to 1000 mg per daily dose of a liquid formulation.

Methylsulfonylmethane (MSM) may be synthesized by methods known to the person skilled in the art. Daily intake of methylsulfonylmethane by a human adult (weighing approximately 70 kg) is preferably between 100 and 7000 mg per day, more preferably between 500 and 2000 mg/day, most preferably between 250 and 750 mg per day.

A nutraceutical preferably comprises 5 mg to 3000 mg of MSM per serving. A pharmaceutical may preferably comprise MSM in an amount from 10 mg to 1000 mg per dosage unit, e.g., per capsule or tablet, or from 250 mg per daily dose to 750 mg per daily dose of a liquid formulation.

Within the framework of the invention SAMe is defined as S-adenosylmethionine. SAMe is commercially available and is preferably dosed between 50 and 3000 mg/day. Examples of amounts used in commercially available products are: 200 mg SAMe (from 400 mg of SAMe-tosylate disulfate); 400 mg S-adenosyl L-methionine (from SAMe); 200 mg S-adenosyl methionine; 400 mg SAMe (as S-adenosylmethionine 1,4-butanedisulfonate).

A nutraceutical preferably comprises 5 mg to 1000 mg of SAMe per serving. A pharmaceutical may preferably comprise SAMe in an amount from 10 mg to 1000 mg per dosage unit, e.g., per capsule or tablet, or from 10 mg per daily dose to 3000 mg per daily dose of a liquid formulation.

Collagen hydrolysate is a protein mixture which may be extracted from animal cartilage. It is commercially available from many supplement companies. Collagen hydrolysate and collagen are commercially available and the daily intake thereof by a human adult (weighing approximately 70 kg) is preferably between 500 and 10000 mg per day, preferably between 2000 and 8000 mg per day.

Unhydrolyzed or undenatured collagen, herein referred to as 'collagen' may be isolated from chicken sternum by methods known to the person skilled in the art.

A nutraceutical preferably comprises between 5 mg and 5000 mg of collagen or collagen hydrolysate per serving. A pharmaceutical composition may preferably comprise collagen in an amount from 10 mg to 1000 mg per dosage unit, e.g., per capsule or tablet, or from 10 mg per daily dose to 5000 mg per daily dose of a liquid formulation.

The term "ascorbyl phosphate" as used herein denotes metal salts of mono- and poly-phosphoric acid esters of ascorbic acid wherein the phosphorylated hydroxy group of the ascorbic acid molecule features one or more phosphoric acid (phosphate) units, and metal cations, e.g. sodium and/or magnesium or calcium ions, are also present. The term "poly" generally denotes 2-10, preferably 2-4, phosphate units. The ascorbyl phosphates may also be referred to in general as "ascorbyl (poly)phosphates" to embrace both mono- and polyphosphates. Typical ascorbyl phosphates for use in the present invention are L-ascorbic acid phosphate ester salts such as sodium ascorbyl phosphate, potassium ascorbyl phosphate, magnesium ascorbyl phosphate, calcium ascorbyl phosphate and sodium magnesium L-ascorbyl-2-monophosphate. Commercially available ascorbyl phosphates comprise trisodium L-ascorbyl-2-monophosphate which is available as STAY-C®50 from DSM Nutritional Products AG, (4303 Kaiseraugst, Switzerland) and magnesium L-ascorbyl phosphate available from Showa Denko) and sodium magnesium L-ascorbyl-2-monophosphate and L-ascorbic acid-monophosphate which is available as ROVIMIX® STAY-C® 35 from DSM Nutritional Products AG, (4303 Kaiseraugst, Switzerland). The preferred ascorbyl phosphate for the purposes of the present invention is trisodium L-ascorbyl-2-monophosphate. The ascorbyl phosphate may be incorporated into the nutraceutical, pharmaceutical, cosmetic or dermatological preparations in many dosage amounts as known to the person skilled in the art.

Lycopene ($\psi,\psi$ carotene; $C_{40}H_{56}$; CAS-number: 502-65-8) belongs to the carotenoid family and contains 11 conjugated double-bonds and an additional two non-conjugated carbon-carbon double-bonds. Lycopene is one of the major dietary carotenoids and is found in various fruits and vegetables, especially in tomatoes and tomato products. It also occurs e.g. in water melon, pink grapefruit, guava.

Lycopene is preferably used in a concentration so that the daily consumption by an animal including humans (e.g. weighing about 70 kg) is in the range of from 0.05 mg/day to 50 mg/day, more preferably from 0.5 mg/day to 30 mg/day. A nutraceutical composition preferably comprises 0.05 mg to 50 mg of lycopene per serving. If the composition is a pharmaceutical composition such composition may preferably comprise Lycopene in an amount from 0.5 mg to 50 mg per dosage unit, e.g., per capsule or tablet, or a liquid formulation.

BRIEF DESCRIPTION OF THE DRAWINGS

FIG. 1 relates to chemical structures as follows: oleuropein (I); oleuropein aglycone (II), 2-hydroxy-4-methoxy-3-(2-hydroxy-3-methyl-3-butenyl)-6-(2-phenylethyl)-benzoic acid (III), Arnorfrutin B (IV), Arnorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula as drawn (X), 2-hydroxy-4-methoxy-5-(2-hydroxy-3-methyl-3-butenyl)-6-(2-phenylethyl)-benzoic acid (XI), cardol diene (XII), and cardol triene (XIII).

The chemical structure of cardol diene is given in FIG. 1, structure (XII). The chemical structure of cardol triene is given in FIG. 1, structure (XIII)

Preferably cardol diene (XII) is used in the composition of the present invention.

Cardol diene (XII) and/or cardol triene (XIII) is preferably used in a concentration so that the daily consumption by an animal including humans (e.g. weighing about 70 kg) is in the range of from 1 mg/day to 2000 mg/day, preferably from 5 mg/day to 500 mg/day. A nutraceutical composition preferably comprises between 0.2 mg and 1000 mg of cardol diene (XII) and/or cardol triene (XIII) per serving. In case of a pharmaceutical composition the amount of cardol diene (XII) and/or cardol triene (XIII) may be selected from 0.5 mg and 2000 mg per dosage unit, e.g., per capsule or tablet, or between 1 mg per daily dose and 3000 mg per daily dose of a liquid formulation.

Cardol diene (XII) and/or cardol triene (XIII) may also be used in the form of an extract for instance an—preferably organic phase or supercritical fluid—extract of the cashew plant (*Anacardium occidentale*)) or a part of the cashew plant, for example in the form of an extract of cashew fruit.

Cardol diene (XII) and/or cardol triene (XIII) may be synthesized or extracted and/or purified by methods known to the person skilled in the art.

Cardol diene (XII) and/or cardol triene (XIII) are preferably derived from the cashew plant that may be obtained from conventional and commercially available sources such as growers. A number of phenolic compounds are found in *Anacardium occidentale*, the cashew nut, the cashew nut shell, the cashew apple, and from various *Toxicodendron* species like *T. radicans, T diversilobum*, also from *Rhus verniciflua*, and *Melanorrhoea usitata*.

Cardol diene (XII) and/or cardol triene (XIII) as employed herein may be prepared by a number of methods known in the art. The mentioned plants may be processed by any suitable means to obtain the compositions described. For example, cashew apple may be extracted to obtain a mixture. Cardol diene (XII) and/or cardol triene (XIII) may be obtained directly from the mixture or the mixture may be fractionated and/or purified to obtain cardol diene (XII) and/or cardol triene (XIII). The compositions may be fractionated and/or purified by a number of methods known to the person skilled in the art. Examples of fractionating methods include partitioning with an organic solvent, chromatography, for example high pressure liquid chromatography (HPLC) or the use of supercritical fluids.

Cardol diene (XII) and/or cardol triene (XIII) can for example be obtained by extraction of dried plant material of *Anacardium occidentale* with methanol: methyl tert butyl ether (9:1) and by subsequent fractionation of the thus obtained crude extract by preparative HPLC in a buffered solvent system.

Cashew fruit extract is preferably used in such an amount that the amount of cardol diene (XII) and/or cardol triene (XIII) is as described above.

Hydroxytyrosol and/or oleuropein (I) may also be combined with *Glycyrrhiza foetida*. The term '*Glycyrrhiza foetida*' encompasses all parts of the plants derived from *Glycyrrhiza foetida* as well as extracts derived thereof.

Hydroxytyrosol and/or oleuropein (I) may also be combined with compounds isolated from *Glycyrrhiza foetida* such as 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), Cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), more preferably enriched in at least one compound from the group of cannabigerolic acid monomethyl ether, 2-hydroxy-4-methoxy-3-(2-hydroxy-3-methyl-3-butenyl)-6-pentyl-benzoic acid and 3-methoxy-2-(3-methyl-2-butenyl)-5-(2-phenylethyl)-phenol.

*Glycyrrhiza foetida* as a whole or parts thereof such as the seedlings, the young plants, the leaves, the flowers (optionally in dried or ground form) or seeds may be used in dried and grinded form or may be extracted conventionally with solvents like ethanol, dichloromethane at reflux temperature or at lower temperature. Alternatively, it may be extracted with supercritical fluids like SF carbon dioxide or by steam distillation of the plant with water followed by sampling of the distilled organic part. Sampling may for example be done by extraction with an organic solvent like dichloromethane, ethylacetate etc. Subsequent removal of the solvent gives the desired *Glycyrrhiza foetida* extract.

Optionally, the thus obtained *Glycyrrhiza foetida* extract may be subjected to further processing steps to enrich the content of specific compounds to give an extract of *Glycyrrhiza foetida* e.g. enriched in 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), Cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), more preferably enriched in at least one compound from the group of cannabigerolic acid monomethyl ether, 2-hydroxy-4-methoxy-3-(2-hydroxy-3-methyl-3-butenyl)-6-pentyl-benzoic acid and 3-methoxy-2-(3-methyl-2-butenyl)-5-(2-phenylethyl)-phenol. Compounds III to XI are depicted in FIG. 1.

*Glycyrrhiza foetida* extracts enriched in at least one compound selected from the group of cannabigerolic acid monomethyl ether, 2-hydroxy-4-methoxy-3-(2-hydroxy-3-methyl-3-butenyl)-6-pentyl-benzoic acid and 3-methoxy-2-(3-methyl-2-butenyl)-5-(2-phenylethyl)-phenol are preferred.

All compounds (III)-(XI) can e.g. be obtained by extraction of dried plant material of *Glycyrrhiza foetida* with methanol: methyl tert butyl ether (MTB) (9:1) and by subsequent fractionation of the thus obtained crude extract by preparative HPLC, for example in a buffered solvent system or can be synthesized. Examples of fractionating methods include partitioning with an organic solvent, chromatography, for example high pressure liquid chromatography (HPLC) or the use of supercritical fluids. Of course the compounds of (III)-(XI) may also be accessible via chemical synthesis)

Preferably compounds (III) to (XI) are used in the form of an extract derived from *Glycyrrhiza foetida*.

The *Glycyrrhiza foetida* extract and/or the compounds contained therein are preferably derived from *Glycyrrhiza foetida* that may be obtained from conventional and commercially available sources such as growers.

The *Glycyrrhiza foetida* as well as the extracts derived thereof are preferably used so that the daily consumption by an animal including humans (e.g. weighing about 70 kg) is in the range of from 0.5 mg/day to 2000 mg/day, preferably from 5 mg/day to 500 mg/day. A nutraceutical composition preferably comprises 0.5 mg to 1000 mg of a *Glycyrrhiza foetida* extract. If the composition is a pharmaceutical composition such composition may comprise the *Glycyrrhiza foetida* extract in an amount from preferably 1 mg to 2000 mg per dosage unit, e.g., per capsule or tablet, or from 1 mg per daily dose to 3000 mg per daily dose of a liquid formulation.

The individual compounds isolated from the *Glycyrrhiza foetida* are preferably used in a concentration so that the daily consumption by an animal including humans (e.g. weighing about 70 kg) is in the range of from 0.5 mg/day to 2000 mg/day, preferably from 5 mg/day to 500 mg/day. A nutraceutical composition preferably comprises 0.5 mg to 1000 mg of such a compound. If the composition is a pharmaceutical composition such composition may comprise one or more of the compounds contained in *Glycyrrhiza foetida* in an amount from preferably 1 mg to 2000 mg per dosage unit, e.g., per capsule or tablet, or from 1 mg per daily dose to 3000 mg per daily dose of a liquid formulation.

If the individual compounds are used in form of a *Glycyrrhiza foetida* extract, the extract is preferably used in such an amount that the amount of individual compound(s) is as described above.

Extracts of *Harpagophytum procumbens* (Devil's claw) are on the market. The active ingredient in Devil's Claw is a glycoside called harpagoside. Other constituents of Devil's Claw include beta-sitosterol, harpagide, procumbine, sugars, gum resin and bitter ingredients. Devil's Claw's dosage can easily be determined by the person skilled in the art and is preferably within the same range as on the market.

Milk protein concentrate includes milk protein hydrolysates and is commercially available for example as Micro-Lactin™ from Brandenburg nutrition or as Peptopro from DSM Food Specialities. It's dosage can easily be determined by the person skilled in the art and is preferably within the same range as on the market.

Horse chestnut extract refers to an extract obtained from *Aesculus hippocastanum* comprising a mixture of saponins.

Other examples of compounds with which hydroxytyrosol and/or oleuropein (I) may be combined to get a synergistic effect are solubilized keratin, celery seed extract, cetylated fatty acids, carnitine thymoquinone, lutein, zeaxanthin and β-cryptoxanthin.

In another aspect, the invention relates to a cosmetic or dermatological preparation (the latter preparation are a specific type of a pharmaceutical) comprising an effective amount of the composition of the invention and a cosmetically or dermatologically acceptable carrier.

The cosmetic or dermatological composition may further comprise conventional cosmetic respectively dermatological adjuvants and/or additives and/or additional active ingredients.

Preferably the cosmetic or dermatological preparations are skin care formulations for the treatment, co-treatment or prevention of inflammation of the skin, in particular of sunburn caused by UV-radiation, of contact dermatitis (particularly diaper area dermatitis), atopic dermatitis, xerosis, eczema, rosacea, seborrhea, psoriasis, neurodermitis, thermal burns, photoageing or for the treatment, co-treatment or prevention of impure skin. Examples of impure skin include pimples, acne and other skin impurities with an inflammatory aspect.

The term "effective amount" means preferably at least 0.001% of each active agents as listed above based on the total weight of the cosmetic or dermatological composition. Preferably, the cosmetic or dermatological preparations comprise the active agents selected from the list above in an amount between 0.01 wt.-% and 20 wt.-%, more preferably between 0.05 and 10 wt.-%, still more preferably between 0.1 and 5 wt.-%.

The amount of the cosmetic or dermatological preparation which is to be applied to the skin depends on the concentration of the active ingredients in the preparation and the desired cosmetic or pharmaceutical effect. For example, the application can be such that a crème is applied to the skin. A crème is usually applied in an amount of about 1 to 2 mg crème/cm² skin. The amount of the composition which is applied to the skin is, however, not critical, and if with a certain amount of applied composition the desired effect cannot be achieved, a higher concentration of the active preparations which contain more active ingredient might be employed.

The invention also relates to the use of the cosmetic preparation for the cosmetic treatment, co-treatment or prevention of inflammation of the skin, in particular for the cosmetic treatment, co-treatment or prevention of sunburn, contact dermatitis (particularly diaper area dermatitis), atopic dermatitis, xerosis, eczema, rosacea, seborrhea, psoriasis, neurodermitis, thermal burns or photoageing.

Also, the invention relates to a method for the treatment, co-treatment or prevention of inflammation of the skin, in particular of sunburn in humans, of impure skin such as for example acne or of photoageing which is associated with chronic skin inflammation, said method comprising the step of administering an effective amount of the dermatological composition according to the invention to humans, which are in need thereof. Also, the invention relates to a method for cosmetic treatment, co-treatment or prevention of inflammation of the skin, in particular of sunburn or of impure skin by a cosmetic preparation according to the invention. Sunburn prevention is preferably achieved with topical application comprising the composition of the invention preferably in combination with suitable light screening agents.

The cosmetic or dermatological preparations according to the invention may be in the form of a suspension or dispersion in solvents or fatty substances, or alternatively in the form of an emulsion or micro emulsion (in particular of O/W or W/O type, O/W/0 or W/O/W-type, wherein O stands for oil phase and wherein W stands for water phase), such as a cream, a paste, a lotion, a thickened lotion or a milk, a vesicular dispersion in the form of an ointment, a gel, a solid tube stick or an aerosol mousse, and may be provided in the form of a mousse, foam or a spray foams, sprays, sticks or aerosols or wipes. Examples of cosmetic or dermatological preparations are skin care preparations, in particular, body oils, body lotions, body gels, treatment creams, skin protection ointments, moisturizing gels, moisturizing sprays, revitalizing body sprays, after sun preparations or sunscreen formulations.

The cosmetic or dermatological composition for the treatment, co-treatment or prevention of inflammation of the skin, such as for example sunburn, photoageing or impure skin may be in a form that is conventional for oral administration, examples of which are described above and also include beauty foods and supplements.

The cosmetic or dermatological preparations of the invention for instance as sunscreen formulations or after sun preparations may further comprise the usual cosmetic respectively dermatological adjuvants and/or additives such as preservatives/antioxidants, fatty substances/oils, water, organic solvents, silicones, thickeners, softeners, emulsifiers, additional light screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives active ingredients or any other ingredients usually formulated into cosmetics.

Light screening agents which may be incorporated into cosmetic or dermatological preparations of the invention for instance sunscreen formulations are advantageously selected from IR, UV-A, UV-B, UV-C and/or broadband filters. Examples of UV-B or broad spectrum screening agents, i.e. substances having absorption maximums between about 290 and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2', 4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethyl ene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanol amine salts, diethanol amine salts and the like; salicylate derivatives such as isopropylbenzyl salicylate, benzyl salicylate, butyl salicylate, ethylhexyl salicylate (PARSOL® EHS, NEO Heliopan OS), isooctyl salicylate or homomethyl salicylate (homosalate, PARSOL® HMS, NEO Heliopan OS) and the like; triazine derivatives such as ethylhexyl triazone (Uvinul T-150), diethylhexyl butamido triazone (Uvasorb HEB). Encapsulated UV-filters such as encapsulated ethylhexyl methoxycinnamate (Eusolex UV-pearls) or microcapsules loaded with UV-filters as e.g. disclosed in EP 1471995 and the like. Inorganic compounds are pigments such as microparticulated TiO$_2$, ZnO and the like. The term "microparticulated" refers to a particle size from about 5 nm to about 200 nm, particularly from about 15 nm to about 100 nm. The TiO$_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV A screening agents i.e. substances having absorption maxima between about 320 and 400 nm may be organic or inorganic compounds e.g. dibenzoylmethane derivatives such as 4-tert. butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (TINOSORB M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1. Pigments such as microparticulated ZnO or TiO2 and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability, it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

Active ingredients which may be included in the cosmetic or dermatological preparations of the invention are for example vitamins and derivatives thereof, for example tocopherol, tocopherol acetate, ascorbic acid, ascorbyl phosphate, vitamin Q, D, and K, retinol, retinal, retinoic acid, retinol acetate, retinol palmitate, biotin, carotenoid derivatives such as beta-carotene, lycopene, astaxanthin, vegetable extracts, antibacterial ingredients, instable amino acids comprising dipeptides, oligopeptides and polypeptides such as methionine, cysteine, cystine, tryptophan, phenylalanine, tyrosine, phenols, polyphenols or flavanoids, bisabolol, allantoin, phytantriol, panthenol, AHA acids, ubiquinones such as coenzyme Q 10, ceramides, pseudoceramides, essential oils, plant extracts deoxyribonucleic acid, phytanic acid.

The necessary amounts of the cosmetic and dermatological adjuvants, additives and/or additional active ingredients can, based on the desired product, easily be chosen by a person skilled in the art and will be illustrated in the examples, without being limited hereto.

In yet another embodiment, the invention relates to the use of hydroxytyrosol and/or oleuropein (I) for enhancing the anti-inflammatory activity of one or several compounds selected from the group of ligustilide, oleuropein aglycone (II), tyrosol, extract from the bark of *Magnolia officinalis*, magnolol, honokiol, genistein, resveratrol, EGCG, methylsulfonylmethane, SAMe, collagen hydrolysate, collagen, ascorbyl phosphate, lycopene, lutein, zeaxanthin, β-cryptoxanthin, Devil's Claw, milk protein concentrate, solubilized keratin, celery seed extract, cetylated fatty acids, carnitine, thymoquinone, 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), cardol diene (XII), cardol triene (XIII), cashew fruit extract, boswellic acid, carnosic acid, ursolic acid, horse chestnut extract, diosmetin, tryptanthrin, diosgenin, curcumin and derivatives, *Glycyrrhiza foetida* and white willow bark extract, in particular of ligustilide, honokiol, genistein, resveratrol and EGCG.

Preferably, the invention relates to the use of hydroxytyrosol and/or oleuropein (I), in particular hydroxytyrosol, for enhancing the anti-inflammatory activity of one or several compounds selected from the group of ligustilide, honokiol, genistein, resveratrol and EGCG.

Thus, the invention relates to the use of hydroxytyrosol and/or oleuropein (I), in particular hydroxytyrosol, for enhancing the anti-inflammatory activity of ligustilide.

In another embodiment invention relates to the use of hydroxytyrosol and/or oleuropein (I), in particular hydroxytyrosol, for enhancing the anti-inflammatory activity of honokiol. Most preferably, honokiol is used in the form of an extract from the bark of *Magnolia officinalis* comprising honokiol and magnolol.

In a further embodiment the invention relates to the use hydroxytyrosol and/or oleuropein (I), in particular hydroxytyrosol, for enhancing the anti-inflammatory activity of genistein.

In an additional embodiment the invention relates to use of hydroxytyrosol and/or oleuropein (I), in particular hydroxytyrosol, for enhancing the anti-inflammatory activity of resveratrol.

In an additional embodiment the invention relates to use of hydroxytyrosol and/or oleuropein (I), in particular hydroxytyrosol, for enhancing the anti-inflammatory activity of EGCG.

In another embodiment the invention relates to a method of enhancing the efficacy of hydroxytyrosol and/or oleuropein (I) which comprises adding to a composition containing hydroxytyrosol and/or oleuropein (I) an effective amount of one or several components selected from the group of ligustilide, oleuropein aglycone (II), tyrosol, extract from the bark of *Magnolia officinalis*, magnolol, honokiol, genistein, resveratrol, EGCG methylsulfonylmethane, SAMe, collagen hydrolysate, collagen, ascorbyl phosphate, lycopene, lutein, zeaxanthin, β-cryptoxanthin, Devil's Claw, milk protein concentrate, solubilized keratin, celery seed extract, cetylated fatty acids, carnitine, thymoquinone, 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), cardol diene (XII), cardol triene (XIII), cashew fruit extract, boswellic acid, carnosic acid, ursolic acid, horse chestnut extract, diosmetin, tryptanthrin, diosgenin, curcumin and derivatives, *Glycyrrhiza foetida* and white willow bark extract, in particular of ligustilide, honokiol, genistein, resveratrol and EGCG. The term 'an effective amount' refers to an amount necessary to obtain a synergistic effect. The dosage may, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired and can be adjusted by a person skilled in the art.

Thus, in a preferred embodiment the invention relates to a method of enhancing the efficacy of hydroxytyrosol and/or oleuropein (I) which comprises adding to a composition containing hydroxytyrosol and/or oleuropein (I) an effective amount of ligustilide.

In another preferred embodiment the invention also relates to a method of enhancing the efficacy of hydroxytyrosol and/or oleuropein (I) which comprises adding to a composition containing hydroxytyrosol and/or oleuropein (I), in particular hydroxytyrosol, an effective amount of honokiol. Most preferably, honokiol is used in the form of an extract from the bark of *Magnolia officinalis* comprising honokiol and magnolol.

In a further preferred embodiment the invention relates to a method of enhancing the efficacy of hydroxytyrosol and/or oleuropein (I), in particular hydroxytyrosol, which comprises adding to a composition containing hydroxytyrosol and/or oleuropein (I) an effective amount of genistein.

In an additional preferred embodiment the invention relates to a method of enhancing the efficacy of hydroxytyrosol and/or oleuropein (I), in particular hydroxytyrosol, which comprises adding to a composition containing hydroxytyrosol and/or oleuropein (I) an effective amount of resveratrol.

In an additional preferred embodiment the invention relates to a method of enhancing the efficacy of hydroxytyrosol and/or oleuropein (I), in particular hydroxytyrosol which comprises adding to a composition containing hydroxytyrosol and/or oleuropein (I) an effective amount of EGCG.

It has been found that the compositions according to the invention are also suitable for the treatment, co-treatment or prevention of cartilage degradation or cartilage damage in joints and as such for treatment of the cartilage degradation component of joint disorders, for example degenerative joints disorders such as osteoarthritis; or sport injuries. Cartilage degradation is defined within the framework of the invention as a metabolic disorder of joint cartilage characterized by increased production of cartilage-degrading enzymes such as matrix metalloproteases.

Osteoarthritis is a chronic degenerative disease of the joint of non-inflammatory origin, which develops by wear and tear of the joints during aging and results in pain and diminished joint function. Symptoms of osteoarthritis include pain, stiffness and loss of mobility in one or more joints. Excessive joint loading increases the risk of osteoarthritis, hence osteoarthritis mostly affects the weight-bearing joints such as spine, knees and hips, but thumb and finger joints may also be affected. Joint disorders can also results from injury, i.e. microdamage or blunt trauma, fractures, damage to tendons, menisci or ligaments or can be the result of excessive mechanical stress or other biomechanical instability resulting from for example an injury or obesity.

Joint disorders due to cartilage degradation are leading causes of disability and dysfunction in the elderly; almost 80% of people over age 60 show some evidence of these disorders. Age, genetic factors, muscle disuse and weakness, trauma, obesity and anatomical abnormalities contribute to the development of the disorder.

Joint disorders are difficult to treat. Up till now, treatment was largely limited to addressing the symptoms mainly with non-steroidal anti-inflammatory drugs. The drugs are given to control the pain and to restrain swelling, but do not prevent or treat damage to the cartilage. The patients experiencing severe cartilage damage frequently require surgery, including joint replacement surgery. Therefore, there was a great need for agents that treat or prevent cartilage loss and damage, which need has been solved by the present invention.

The composition of the present invention may have one or more of the following properties: it maintains and/or improves joint health, it prevents joint stiffness, it promotes joint mobility, it provides supple and/or flexible joints, it lubricates the joints, it relieves arthritis pain, it lessens joint problems, it provides joint care, it treats or prevents joint degradation, it provides joint integrity, it retards or prevents the progression of joint damage, it supports joint function, it promotes joint health and function, it naturally supports joint health and mobility for active individuals, it maintains the active flexibility of joints, it promotes joint flexibility and promotes joint mobility.

Thus, further objects of the present invention are:
- Use of a composition according to the invention as cartilage-regenerating and maintaining agent.
- Use of a composition according to the invention for maintenance of joint health.
- Use of a composition according to the invention (for the manufacture of a composition) for the maintenance and regeneration of articular cartilage.
- A method for the regeneration and/or maintenance of (articular) cartilage in a mammal which comprises administering to a mammal in need of such regeneration and/or maintenance an effective amount of a composition according to the invention.

The invention will now be elucidated by way of the following examples, without however being limited thereto.

EXAMPLES

In the following examples, "Group (A)" is defined as the following group of compounds: ligustilide, oleuropein aglycone (II), tyrosol, extract from the bark of *Magnolia officinalis*, magnolol, honokiol, genistein, resveratrol, EGCG methylsulfonylmethane, SAMe, collagen hydrolysate, collagen, ascorbyl phosphate, lycopene, lutein, zeaxanthin, β-cryptoxanthin, Devil's Claw, milk protein concentrate, solubilized keratin, celery seed extract, cetylated fatty acids, carnitine, thymoquinone, 2-hydroxy-4-methoxy-3-(2-hydroxy-3-methyl-3-butenyl)-6-(2-phenylethyl)-benzoic acid (III), Amorfrutin B (IV), Amorfrutin A (V), 2-hydroxy-4-methoxy-3-(3-methyl-2-butenyl)-6-pentyl-benzoic acid (VI), cannabigerolic acid monomethyl ether (VII), 2-hydroxy-4-methoxy-3-(2-hydroxy-3-methyl-3-butenyl)-6-pentyl-benzoic acid (VIII), 3-methoxy-2-(3-methyl-2-butenyl)-5-(2-phenylethyl)-phenol (IX), the compound of formula (X) and 2-hydroxy-4-methoxy-5-(2-hydroxy-3-methyl-3-butenyl)-6-(2-phenylethyl)-benzoic acid (XI), cardol diene (XII), cardol triene (XIII), cashew fruit extract, boswellic acid, carnosic acid, ursolic acid, horse chestnut extract, diosmetin, tryptanthrin, diosgenin, curcumin and derivatives, *Glycyrrhiza foetida* and white willow bark extract.

Hydroxytyrosol is commercially available from Cayman Chemicals or was synthesized by DSM Nutritional Products. Resveratrol, ligustilide, EGCG and genistein was synthesized by DSM Nutritional Products. *Magnolia* Bark extract was from Novanat Bioresources Co. Ltd. China and contained according to the specification >80% Magnolol and Honokiol. Oleuropein, Magnolol and Honokiol may be purchased at Wako Pure Chemical Industries, Ltd., Japan, Apin Chemicals Ltd, UK, Sigma, or ChromaDex or were synthesized by DSM Nutritional Products.

Example 1

Synergistic Effect

The anti-inflammatory effects combinations of OH-tyrosol or oleuropein and representatives of other groups of natural substances (isoflavones, catechins, phtalides, hydroxylated biphenyls) were evaluated in activated macrophages by determining the inhibition of the synthesis of nitric oxide and/or pro-inflammatory prostaglandins (PG). $PGE_2$ plays a critical role in the inflammation process, while nitric oxide (NO) is a hallmark of inflammation in various chronic inflammatory diseases including various forms of arthritis, gastro-intestinal diseases and metabolic syndrome. The compounds used in the experiment were dissolved in DMSO in concentrated form and did not contain byproducts that interfered with the assays. Final vehicle (DMSO) concentration did not exceed 0.2% v/v in the assays.

The anti inflammatory effect of compounds was tested in cellular assays using a murine macrophage indicator cell line, RAW267.7, which was purchased from American Type Culture Collection, (ATCC) and cultured in DMEM according to the protocol provided by ATCC. Cells (~50,000/well) were seeded into flat-bottomed microtiter plates and cultured for one day. Cells were then starved in complete medium containing 0.25% FCS (D-025). After overnight culture, medium was removed and replaced by 100 µL of D-025 containing the test compounds at twice the final concentration. Subsequently, 100 µL of D-025 containing 2 µg/ml LPS was added (i.e. final LPS concentration of 1 µg/ml) and the cells cultured for 24 hours. Substances were usually tested in a concentration range from 0.2 to 50 µM (or µg/ml in the case of extracts) in two-fold dilution steps. Concentrations of nitrite which was generated from nitric oxide released by cells were determined by the Griess reaction using sodium nitrite as standard (see e.g Imai et al. Biochem Biophys Res Comm, 197, 105 [1993]). Briefly, 50 µl of supernatant was mixed with Griess reagent 1 (25 µL) and Griess reagent 2 (25 µL), centrifuged and the optical density at 540 nm determined. $PGE_2$ secreted into the cell culture medium was determined by EIA obtained from Cayman Chemicals (Ann Harbor, Wis., USA) and used according to the manufacturer's instructions. $IC_{50}$ values were calculated using a two-parametric least-square fitting equation $[y=A+((B-A)/(1+((C-x)^D))]$ for best-fit curves (Excel fit software program).

In Table 1 it is shown that individually, all substances inhibited the production of inflammatory mediators. This is indicated by $IC_{50}$ values, which vary between substances reflecting substance-specific biological potencies.

In Table 2 it is shown that hydroxytyrosol (OH-Tyrosol) or oleuropein when combined with resveratrol, ligustilide, EGCG, honokiol, genistein or *Magnolia* Bark extract synergistically inhibits nitric oxide production. A positive value for Δ (observed-additive) means that the two substances outperform the inhibitory power of the two individual components of the mixture. With 'observed' is meant the actual observed inhibition. With 'additive' is meant the theoretical sum of the inhibition of the two compounds

TABLE 1

$IC_{50}$ values for single substances

| Substance | $IC_{50}$ $PGE_2$ | $IC_{50}$ Nitric Oxide |
|---|---|---|
| OH-Tyrosol | 24 ± 3 µmol/L | 28 ± 2 µmol/L |
| Oleuropein | 60 ± 10 µmol/L | 52 ± 5 µmol/L |
| Resveratrol | 24 ± 2 µmol/L | 31 ± 2 µmol/L |
| EGCG | 35 ± 3 µmol/L | 33 ± 2 µmol/L |
| Ligustilide | 10 ± 2 µmol/L | 15 ± 1 µmol/L |
| Genistein | 4.6 ± 0.6 µmol/L | 37 ± 2 µmol/L |
| Magnolia Bark | 1.2 ± 0.4 µg/mL | 3.6 ± 0.5 µg/mL |
| Honokiol | 1.0 ± 0.2 µmol/L | 8 ± 1 µmol/L |

TABLE 2

Synergistic effects on production of nitric oxide

| Substance | Concentration | % inhibition of NO production | Δ* |
|---|---|---|---|
| OH-Tyrosol (OT) | 12.5 μmol/L | 33 | |
| Resveratrol (RES) | 12.5 μmol/L | 19 | |
| OT + RES | 12.5 μmol/L + 12.5 μmol/L | 99 | 47 |
| OH-Tyrosol (OT) | 12.5 μmol/L | 33 | |
| Ligustilide (LIG) | 12.5 μmol/L | 38 | |
| OT + LIG | 12.5 μmol/L + 12.5 μmol/L | 99 | 28 |
| OH-Tyrosol (OT) | 12.5 μmol/L | 33 | |
| EGCG | 12.5 μmol/L | 12 | |
| OT + EGCG | 12.5 μmol/L + 12.5 μmol/L | 51 | 6 |
| OH-Tyrosol (OT) | 12.5 μmol/L | −2 | |
| Honokiol (HO) | 12.5 μmol/L | 66 | |
| OT + HO | 12.5 μmol/L + 12.5 μmol/L | 78 | 14 |
| OH-Tyrosol (OT) | 6.25 μmol/L | 7 | |
| Genistein (GEN) | 25 μmol/L | 40 | |
| OT + GEN | 6.25 μmol/L + 25 μmol/L | 54 | 7 |
| OH-Tyrosol (OT) | 12.5 μmol/L | 16 | |
| Magnolia Bark (MB) | 0.25 μg/mL | −4 | |
| MB + OT | 12.5 μmol/L + 0.25 μmg/L | 23 | 11 |
| Oleuropein (OLE) | 12.5 μmol/L | 8 | |
| Resveratrol (RES) | 12.5 μmol/L | 3 | |
| OLE + RES | 12.5 μmol/L + 12.5 μmol/L | 39 | 28 |
| Oleuropein (OLE) | 3.125 μmol/L | 2 | |
| Ligustilide (LIG) | 3.125 μmol/L | 28 | |
| OLE + LIG | 3.125 μmol/L + 3.125 μmol/L | 53 | 23 |

*(observed - additive; Additive = Σ (compound A (e.g. OT/OLE) + compound B (e.g. RES/LIG etc)

Example 2

Synergistic Effects Observed with a Combination of Lycopene Resveratrol and OH-tyrosol In a methodological approach that was similar to that described for Example 1, the synergistic effect of lycopene, resveratrol and OH-tyrosol was tested on the inflammatory response. Dose-dependent effects of each substance on the production of nitric oxide or PGE$_2$ in macrophages were determined. Unlike resveratrol or OH-tyrosol, lycopene had no anti-inflammatory effect (at <8 μmol/L). In the concentration range where synergistic effects were revealed, single compounds had low or no inhibitory effect on the production of inflammatory mediators. Yet, unexpectedly the combination significantly reduced NO produced by activated macrophages. Similar features were observed with regard to the effect on PGE$_2$ production.

TABLE 3

Synergistic effects on production of nitric oxide

| Substance | Concentration | % inhibition of NO production | Δ* | IC$_{50}$ of pure compound |
|---|---|---|---|---|
| Lycopene (Ly) | 0.5 μmol/L | 4 | — | >8 μmol/L |
| Resveratrol (Res) | 3.13 μmol/L | −2 | — | 19.3 μmol/L |
| OH—tyrosol (OT) | 3.13 μmol/L | −4 | — | 24.1 μmol/L |
| Ly + Res + OT | (0.5 + 3.13 + 3.13) μmol/L | 17 | 15 | Not applicable |

*observed - additive; Additive = Σ (Ly + Res + OT)

TABLE 3

Synergistic effects on PGE$_2$ production

| Substance | Concentration | % inhibition of PGE$_2$ production | Δ* | IC$_{50}$ of pure compound |
|---|---|---|---|---|
| Lycopene (Ly) | 0.25 μmol/L | −5 | — | >8 μmol/L |
| Resveratrol (Res) + | 1.56 μmol/L + | 23 | — | 23.4 μmol/L |
| OH— tyrosol (OT) | 1.56 μmol/L | | — | 22.7 μmol/L |
| Ly + Res + OT | (0.25 + 1.56 + 1.56) μmol/L | 49 | 26 | Not applicable |

*observed - additive; Additive = Σ (Ly + Res + OT)

The data surprisingly showed that a combination of lycopene to resveratrol to OH-tyrosol at a molar ratio of about 1:6:6 exert a synergistic inhibitory effects on production of inflammatory mediators as exemplified for nitric oxide and PGE$_2$.

Example 3

Soft Gelatin Capsule

Soft gelatin capsules are prepared by conventional procedures providing a dose of hydroxytyrosol and/or oleuropein (I) of 200 mg and at least one compound selected from the group of Group (A) as defined above of 50 mg (e.g. EGCG). A suitable daily dose is 1 to 8 capsules.

Other ingredients: glycerol. Water, gelatine, vegetable oil

Example 4

Hard Gelatin Capsule

Hard gelatin capsules are prepared by conventional procedures providing a dose of hydroxytyrosol and/or oleuropein (I) of 400 mg and at least one component selected from the group of Group (A) as defined above of 100 mg (e.g. magnolia bark extract). A suitable daily dose is 1 to 5 capsules.

Other ingredients:
Fillers: lactose or cellulose or cellulose derivatives q.s.
Lubricant: magnesium stearate if necessary (0.5%)

Example 5

Tablet

Tablets are prepared by conventional procedures providing as active ingredient 100 mg of hydroxytyrosol and/or oleuropein (I) per tablet and at least one component selected from the group of Group (A) as defined above of 100 mg Ligustilide, and as excipients microcrystalline cellulose, silicone dioxide (SiO$_2$), magnesium stearate, crospovidone NF (which is a disintegration agent) ad 500 mg.

Example 6

Soft Drink

An orange juice drink coloured with beta-Carotene 10% CWS and with hydroxytyrosol and at least one component selected from the group of Group (A) as defined above may be prepared as follows:

| Ingredients | [g] |
|---|---|
| Sugar syrup 64° Brix | 156.2 |
| Sodium benzoate | 0.2 |
| Ascorbic acid, fine powder | 0.2 |
| Citric acid 50% w/w | 5.0 |
| Pectin solution 2% w/w | 10.0 |
| hydroxytyrosol | 0.5 |
| compound selected from the group of Group (A) as defined above | 0.3 |
| Juice compound* | 30.0 |
| Water to | 250.0 |

Preparation

Dissolve sodium benzoate in water whilst stirring

Continue stirring and add sugar syrup, ascorbic acid, citric acid, pectin solution, juice compound, one after the other. Do not use a high speed mixer Dilute the bottling syrup with (carbonated) water to one liter of beverage

| *Ingredients Juice compound | [g] |
|---|---|
| Orange juice concentrate 65° Brix | 483.3 |
| Lemon Juice Concentrate 45° Brix | 173.3 |
| Oily orange flavour | 5.0 |
| beta-Carotene 10% CWS as 10% stock solution | 10.0 |
| Deionized water | 328.4 |

Preparation of Juice Compound

Add the deionized water to the juice concentrates, stir gently and allow the juice concentrates to hydrate.

Add the oily flavour and beta-Carotene 10% CWS stock solution and pre-emulsify in a rotor-stator-homogenizer.

Homogenize in a high pressure homogenizer at 200 bar.

Example 7

Preparation of a Dermatological Composition Comprising Hydroxytyrosol (Treatment Cream) which May be Used for (Cosmetic) Treatment of Inflammation of the Skin Caused by Sunburn A treatment cream may be prepared with the following ingredients, in the following amounts:

| | Ingredients/INCI Nomenclature | wt. % |
|---|---|---|
| A | Glyceryl Myristate | 2.00 |
| | Hydroxytyrosol | 0.20 |
| | Compound selected from the group of Group (A) as defined above | 0.01 |
| | Cetyl Alcohol | 0.50 |
| | Caprylic/Capric Triglyceride | 5.00 |
| | Diisopropyl Adipate | 5.00 |
| | Tocopheryl Acetate | 2.00 |
| | BHT | 0.05 |
| | Phenoxyethanol & Methylparaben & Ethylparaben & Propylparaben & Butylparaben | 0.60 |
| | Disodium EDTA | 0.10 |
| | Potassium Cetyl Phosphate | 2.00 |
| B | Aqua (deionized water) | ad 100 |
| | Propylene Glycol | 2.00 |
| | Panthenol | 2.00 |
| | Ethanol | 5.00 |
| | Allantoin | 0.20 |
| | Carbomer | 0.30 |
| C | Potassium Hydroxide | 1.50 |
| D | Perfume | q.s. |

Procedure: Heat part A) and B) to 85° C. while stirring. When homogeneous, add part B) to A) under agitation. Cool to about 45° C. while stirring. Add part C). Homogenize at 11000 rpm to achieve a small particle size. Cool to ambient temperature while stirring. Then add part D).

Example 8

O/W Sun Milk

| | Ingredients/INCI Nomenclature | wt. % |
|---|---|---|
| A) | Dimethico DiethylbenzalmalonatePolysilicone-15 | 6.00 |
| | Neo Heliopan AP | 3.00 |
| | Hydrogenated Cocoglycerides | 3.00 |
| | Cetearyl Alcohol | 2.00 |
| | Caprylic/capric Triglyceride | 6.00 |
| | Mineral oil | 2.00 |
| | Tocopheryl Acetate | 1.00 |
| | Isostearyl Alcohol | 4.00 |
| B) | Disodium EDTA | 0.10 |
| | Phenoxyethanol & Methylparaben & Ethylparaben & Propylparaben & Butylparaben | 0.60 |
| | Potassium Cetyl Phosphate | 2.00 |
| | Aqua (e.g. deionized water) | ad 100 |
| | Propylene Glycol | 5.00 |
| | Carbomer | 0.30 |
| | Methylene Bis-Benzotriazolyl Tetramethylbutylphenol | 6.00 |
| | Potassium Hydroxyde | 2.10 |
| C) | HIDROX ® 6% freeze dried powder | 0.20 |
| | Compound selected from the group of Group (A) as defined above | 0.05 |

Procedure: Heat part A) and B) to 85° C. while stirring. When homogeneous, add part B) to A) under agitation. Cool to ambient temperature while stirring and add part C). Homogenize to achieve a small particle size.

Example 9

Sun Milk Waterproofed

| | Ingredients/INCI Nomenclature | wt. % |
|---|---|---|
| A) | Polysilicone-15Dimethico Diethylbenzalmalonate | 6.00 |
| | Butyl Methoxydibenzoylmethane | 2.00 |
| | 4-Methylbenzylidene Camphor | 4.00 |
| | Ethylhexyltriazone | 2.00 |
| | Dimethicone | 1.00 |
| | Cetearyl Alcohol | 2.00 |
| | Hydrogenated Coco-Glycerides | 3.00 |
| | C12-15 Alkyl Benzoate | 6.00 |
| | Dibutyl Adipate | 7.00 |
| | Tocopheryl Acetate | 2.00 |
| | BHT | 0.05 |
| | Disodium EDTA | 0.10 |
| | Phenoxyethanol & Methylparaben & Ethylparaben & Propylparaben & Butylparaben | 0.60 |
| | Cetyl Phosphate DEA | 2.00 |
| B) | Aqua (e.g. deionized water) | ad 100 |
| | Propylene Glycol | 5.00 |
| | Carbomer | 0.30 |
| | Potassium Hydroxide | 1.50 |
| C) | Hydroxytyrosol | 0.05 |
| | Compound selected from the group of Group (A) as defined above | 0.10 |

Procedure: Heat part A) and B) to 85° C. while stirring. When homogeneous, add part B) to A) under agitation. Cool to ambient temperature while stirring and add part C). Homogenize to achieve a small particle size.

Example 10

Sun Milk for Babies and Children

| | Ingredients/INCI Nomenclature | wt. % |
|---|---|---|
| A) | C12-15 Alkyl Benzoate | 5.00 |
| | Stearyl Dimethicone | 2.00 |
| | Cetyl Alcohol | 1.00 |

-continued

| | Ingredients/INCI Nomenclature | wt. % |
|---|---|---|
| | BHT | 0.05 |
| | Glyceryl Myristate | 4.00 |
| | Disodium EDTA | 0.10 |
| | Phenoxyethanol & Methylparaben & Ethylparaben & Propylparaben & Butylparaben | 0.60 |
| | Cetyl Phosphate | 2.00 |
| B) | Aqua (e.g. deionized water) | ad 100 |
| | Carbomer | 0.6 |
| | Glycerine | 3.00 |
| | Potassium Hydroxide | 2.4 |
| C) | Hydroxytyrosol | 0.10 |
| | Compound selected from the group of Group (A) as defined above | 0.01 |

Procedure: Heat part A) and B) to 85° C. while stirring. When homogeneous, add part B) to A) under agitation. Cool to ambient temperature while stirring and add part C). Homogenize to achieve a small particle size.

Example 11

Anti Pimple Skin-Tonic

| | Ingredients/INCI Nomenclature | wt. % |
|---|---|---|
| A) | Alkohol | 15.00 |
| | Glycerin | 3.00 |
| | Aqua (e.g. deionized water) | Ad 100 |
| | Disodium EDTA | 0.10 |
| | HIDROX ® 6% freeze dried powder | 1.00 |
| | Compound selected from the group of Group (A) as defined above | 0.05 |

Procedure: Add all ingredients of part 1 and mix intensively until a homogeneous solution is obtained. Adjust the pH to 6.5 with acetic acid.

Example 12

Anti-Acne Treatment with Stay-C 50

| | Ingredients/INCI Nomenclature | wt. % |
|---|---|---|
| A) | Glyceryl Myristate | 1.50 |
| | Cetyl Alcohol | 1.50 |
| | C12-15 Alkyl Benzoate | 4.00 |
| | Phenoxyethanol & Methylparaben & Ethylparaben & Butylparaben & Propylparaben & Isobutylparaben | 0.80 |
| | Isononyl Isononanoate | 2.00 |
| | Steareth-2 | 1.50 |
| | Steareth-21 | 1.50 |
| 2 | Butylene Glycol | 2.00 |
| | Glycerin | 3.00 |
| | Disodium EDTA | 0.10 |
| | Xanthan Gum | 0.30 |
| | Arcylates/C10-30 Alkyl Acrylate Crosspolymer | 0.25 |
| | Hydroxytyrosol | 1.00 |
| | Aqua (e.g. deionized water) | Ad 100 |
| 3 | Aqua (e.g. deionized water) | 10.00 |
| | Sodium Ascorbyl Phosphate | 3.00 |
| | Sodium Metabisulfite | 0.05 |

Procedure: Heat part 1 up to 85° C.; and heat also part 2 up to 85° C. When both have the same temperature add part 2 to part 1 while homogenizing intensively. Cool down the product to 35° C. while stirring. Now add part 3 and homogenize intensively again. It is generally recommended to use vacuum while producing the emulsion.

Example 13

Protective Day Cream

| | Ingredients/INCI Nomenclature | wt. % |
|---|---|---|
| A) | Polysilicone-15Dimethico Diethylbenzalmalonate | 4.00 |
| | Butyl Methoxydibenzoylmethane | 1.50 |
| | Glyceryl Myristate | 2.00 |
| | Cetyl Alcohol | 0.50 |
| | Caprylic/Capric Triglyceride | 5.00 |
| | Diisopropyl Adipate | 5.00 |
| | Tocopheryl Acetate | 2.00 |
| | BHT | 0.05 |
| | Phenoxyethanol & Methylparaben & Ethylparaben & Propylparaben & Butylparaben | 0.60 |
| | Disodium EDTA | 0.10 |
| | Potassium Cetyl Phosphate | 2.00 |
| B) | Aqua (e.g. deionized water) | ad 100 |
| | Propylene Glycol | 2.00 |
| | Panthenol | 2.00 |
| | Ethanol | 5.00 |
| | Allantoin | 0.20 |
| | Carbomer | 0.30 |
| | Potassium Hydroxide | 1.50 |
| C) | Aqua (e.g. deionized water) | 10.00 |
| | Sodium Ascorbyl Phosphate | 0.50 |
| D) | HIDROX ® 2% spray dried powder | 0.50 |
| | Compound selected from the group of Group (A) as defined above | 0.2 |
| E) | Perfume | q.s. |

Procedure: Heat part A), B) and C) to 85° C. while stirring. When homogeneous, add part B) and C) to A) under agitation. Cool to ambient temperature while stirring and add part D) and E). Homogenize to achieve a small particle size.

Example 14

Dry Dog Feed Comprising Hydroxytyrosol and Genistein

Commercial dry dog food (Hill's Science diet "Canine Maintenance dry" for dogs as supplied by Hill's Pet Nutrition GmbH, Liebigstrasse 2-20, D-22113) is sprayed with an aqueous solution of hydroxytyrosol and genistein in an amount sufficient to administer to a subject a daily dose of 200 mg to 1 g hydroxytyrosol and 0.1 mg to 3 mg genistein per kg body weight. Further Vitamin C and E and beta-carotene are incorporated in an amount sufficient to provide 30 mg vitamin C/kg, and 300 IU vitamin E/kg and 280 mg beta-carotene/kg in the final food composition before extruding the entire blend. The food composition is dried to contain dry matter of about 90% by weight.

Example 15

Wet Cat Food Comprising Hydroxytyrosol and Genistein

Commercial wet cat food (Hill's Science diet "Feline Maintenance wet" for cats as supplied by Hill's Pet Nutrition GmbH, Liebigstrasse 2-20, D-22113) is mixed with HIDROX® 2% spray dried powder in an amount sufficient to administer to a subject a daily dose of 200 mg to 1 g hydroxytyrosol. Further ROVIMIX® STAY-C® 35 available from DSM Nutritional Products AG, Vitamin E and beta-carotene are incorporated in an amount sufficient to provide 30 mg ROVIMIX® STAY-C® 35/kg, and 300 IU vitamin E/kg and 280 mg beta-carotene/kg in the final food composition before cooking the entire blend. The food composition is dried to contain a dry matter of about 90% by weight.

Example 16

Cereal Bar/Non Baked

| Ingredients | Quantity [g] |
|---|---|
| Sugar | 138.0 |
| Water | 54.0 |
| Salt | 1.5 |
| Glucose syrup DE38, 43° Be | 130.0 |
| Invert sugar syrup (74-76%) | 95.0 |
| Sorbitol syrup | 35.0 |
| Palmkernel fat | 60.0 |
| Biscofin N | 40.0 |
| Lecithin | 1.5 |
| Monomuls 90-35-5 (emulsifer) | 2.5 |
| Apple dried and cut | 63.0 |
| Raisins | 27.0 |
| Cornflakes | 100.0 |
| Rice crispies | 140.0 |
| Mini Crispini, Wheat | 90.0 |
| Hazelnut, roasted | 54.0 |
| Skim milk powder | 45.0 |
| Apple flavour 74863-33 | 2.0 |
| Citric acid* | 5.0 |
| HIDROX ® 2% spray dried powder | 1.85 |
| Genistein TG | 0.34 |
| Magnolia bark extract | 0.28 |
| β-Carotene 10% B | 0.77 |
| Yield | 1000.0 |

*used to support the apple flavour

2. Preparation:

| | |
|---|---|
| 2.1 | Premix HIDROX, Genistein TG, magnolia bark extract and β-Carotene 10% B with skim milk powder and place in a Kenwood type mixer |
| 2.2 | Add cornflakes, ricecrispies and gently mix with 2.1. Then add the more humid ingredients as dried apples and raisins. All ingredients are gently mixed in order to ensure a good distribution of the dry ingredients |
| 2.3 | The following ingredients are weight into a separate bowl each Sugar, water, salt Glucose- inverte and sorbitol syrup Biscofin N, Palmkernel fat, Lecithin and Emulsifier |
| 2.3 | Mixture of sugar, water and salt is heated to 110° C. |
| 2.4 | Mixture of the different syrups is heated to 113° C. and cooled in a cold water bath in order to stop the cooking process |
| 2.5 | Solution 2.3 and 2.4 are combined |
| 2.6 | Mixture of Biscofin N, palm kernel fat, lecithin and emulsifier are molten in a water bath at 75° C. |
| 2.7 | Mixture (2.6) of fats is added to the combined sugar solution (2.5). The later should be still hot |
| 2.8 | Flavour and citric acid is added to the liquid mass (2.7) |
| 2.9 | The liquid mass is added to the dry ingredients (2.2) in the Kenwood mixer and mixed well with the dry ingredients |
| 2.10 | The mass is put on a marmor plate and rolled to the desired thickness. Then the mass is cooled down at room temperature |
| 2.11 | Cut into pieces of e.g. one serving size and pack into e.g. aluminium bags |

The invention claimed is:

1. A pharmaceutical composition comprising as active ingredients a combination selected from the group consisting of
a combination of hydroxytyrosol and resveratrol,
a combination of hydroxytyrosol and ligustilide,
a combination of hydroxytyrosol and (−)-epigallocatechin gallate (EGCG),
a combination of hydroxytyrosol and honokiol,
a combination of hydroxytyrosol and genistein,
a combination of hydroxytyrosol and *Magnolia* bark extract,
a combination of oleuropein and resveratrol, and
a combination of oleuropein and ligustilide,
in combination with a pharmaceutically acceptable carrier.

2. The pharmaceutical composition as in claim 1, which is in the form of a powder, tablet, capsule, gel, liquid or solid.

3. A method of treating an inflammatory disorder by administering to an animal including to a human in need thereof an effective amount of a pharmaceutical composition comprising a combination selected from the group consisting of a combination of hydroxytyrosol and resveratrol,
a combination of hydroxytyrosol and ligustilide,
a combination of hydroxytyrosol and (−)-epigallocatechin gallate (EGCG),
a combination of hydroxytyrosol and honokiol,
a combination of hydroxytyrosol and genistein,
a combination of hydroxytyrosol and *Magnolia* bark extract,
a combination of oleuropein and resveratrol, and
a combination of oleuropein and ligustilide.

4. The method as in claim 3, wherein the inflammatory disorder is arthritis.

5. The method as in claim 3, wherein the inflammatory disorder is an inflammation of the skin.

* * * * *